United States Patent
Shi et al.

(10) Patent No.: US 11,047,858 B2
(45) Date of Patent: Jun. 29, 2021

(54) METHOD FOR DETECTING AND TYPING RARE TUMOR CELLS IN BODY FLUID SAMPLE AND KIT THEREFOR

(71) Applicant: Suzhou Junhui Biotechnology Co., Ltd., Suzhou (CN)

(72) Inventors: Qihui Shi, Shanghai (CN); Yuliang Deng, Shanghai (CN); Yin Tang, Shanghai (CN); Zhuo Wang, Shanghai (CN)

(73) Assignee: Suzhou Junhui Biotechnology Co., Ltd., Suzhou (CN)

( * ) Notice: Subject to any disclaimer, the term of this patent is extended or adjusted under 35 U.S.C. 154(b) by 0 days.

(21) Appl. No.: 16/867,177

(22) Filed: May 5, 2020

(65) Prior Publication Data

US 2020/0264180 A1 Aug. 20, 2020

Related U.S. Application Data

(63) Continuation of application No. PCT/CN2018/111546, filed on Oct. 24, 2018.

(30) Foreign Application Priority Data

Nov. 16, 2017 (CN) .......................... 201711139300.8

(51) Int. Cl.
*G01N 33/574* (2006.01)
*G01N 15/14* (2006.01)
(Continued)

(52) U.S. Cl.
CPC ... *G01N 33/57423* (2013.01); *G01N 15/1429* (2013.01); *G01N 33/582* (2013.01); *G01N 2015/0065* (2013.01); *G01N 2015/03* (2013.01)

(58) Field of Classification Search
CPC ........... G01N 33/57423; G01N 33/582; G01N 15/1429; G01N 2015/0065; G01N 2015/03; G01N 2015/1006; G01N 2333/70589
See application file for complete search history.

(56) References Cited

U.S. PATENT DOCUMENTS

| 2003/0152549 A1* | 8/2003 | Palladino, Jr. ..... G01N 33/5008 424/85.1 |
| 2018/0231560 A1* | 8/2018 | Rao ........................ C07K 16/30 |

FOREIGN PATENT DOCUMENTS

| CN | 104122254 A | 10/2014 |
| CN | 105705088 A | 6/2016 |

(Continued)

OTHER PUBLICATIONS

Thekkek et al. (Using a Fluorescently labeled Glucose Analog as an Optical Biomarker for the Early Detection of Cancer in Barrett's Esophagus. Gastroenterology 136 (5): Suppl. 1, p. A647 (May 2009).*

(Continued)

*Primary Examiner* — Gailene Gabel
(74) *Attorney, Agent, or Firm* — Sheppard Mullin Richter & Hampton LLP

(57) ABSTRACT

A method for detecting and typing rare tumor cells having high metabolic activity in a body fluid sample, comprising the following steps: incubating nucleated cells in a body fluid sample with a first metabolic marker and a second metabolic marker capable of producing fluorescence signals; detecting, by means of high-throughput imaging, uptake of all the fluorescence signals of the metabolic markers by cells, so as to determine the energy metabolism mode and intensity of the cells; and identifying and typing, according to the fluorescence signals of the metabolic marker combination, tumor cells having high metabolic activity in the body fluid sample. Further provided is a kit used for the detecting and typing method, comprising a microwell array chip, a first metabolic marker and a second metabolic marker capable of producing fluorescence signals, and fluorescence-labeled antibodies specific to leukocyte common antigen. The method and the kit identify and type energy metabolism modes of rare tumor cells in a body fluid sample based on (Continued)

fluorescence signal characteristics, and the operation is simple and fast, reducing the possibility of losing rare tumor cells.

7 Claims, 1 Drawing Sheet

(51) Int. Cl.
*G01N 33/58* (2006.01)
*G01N 15/00* (2006.01)

(56) References Cited

FOREIGN PATENT DOCUMENTS

| | | |
|---|---|---|
| CN | 105954246 A | 9/2016 |
| CN | 107917869 A | 4/2018 |
| JP | 2002253298 A | 9/2002 |
| JP | 4779115 B2 | 9/2011 |

OTHER PUBLICATIONS

Cancer Foundation of China et al., Relationship Between Tumor and Cell Metabolism and its Clinical Application, Cellular Energetics and Quantum Medicine Secrets Between Energy and Health, 8 pages, 2017.

Hanahan et al., Hallmarks of Cancer: The Next Generation, Cell, 144, 29 pages, 2011.

International Search Report and Written Opinion for PCT/CN2018/111546 dated Jan. 30, 2019, 10 pages. English translation of ISR.

O'Neil et al., Uptake of a Fluorescent Deoxyglucose Analog (2-NBDG) in Tumor Cells, Mol. Imaging Biol., 7:388-392, 2005.

Tang et al., High-throughput Screening of Rare Metabolically Active Tumor Cells in Pleural Effusion and Peripheral Blood of Lung Cancer Patients, PNAS Early Edition, 6 pages, 2017.

Tu et al., Hypoxic Environment and Tumor, 6 pages, 2012.

Zhen et al., Resazurin Method to Detect the Sensitivity of K562 Cells to Several Anti-tumor Drugs, Journal of Mountain Agriculture and Biology, 33(2):064-068, 2014.

* cited by examiner

METHOD FOR DETECTING AND TYPING RARE TUMOR CELLS IN BODY FLUID SAMPLE AND KIT THEREFOR

CROSS-REFERENCE TO RELATED APPLICATIONS

This application is a continuation of International Application No. PCT/CN2018/111546, filed Oct. 24, 2018, which application claims the benefit of Chinese Application No. 201711139300.8, filed Nov. 16, 2017.

TECHNICAL FIELD

The present invention relates to a method for conducting functional typing of rare tumor cells having high metabolic activities in a cancer patient's body fluid sample (such as blood, pleural effusion, peritoneal effusion, cerebrospinal fluid, and the like) based on energy metabolism mode. The invention also relates to a kit for detecting and typing the rare tumor cells having high metabolic activity in the cancer patient's body fluid sample.

BACKGROUND

Malignant tumor, in a process of dissemination, invasion, and metastasis, is often accompanied by entrance of tumor cells into a body fluid such as blood, pleural effusion, peritoneal effusion, cerebrospinal fluid and the like. Therefore, the detection of these tumor cells in the body fluid samples is a high-level visual evidence for determination of the presence, or even metastasis, of the tumor, presenting an explicit clinical significance. However, the tumor cells in these body fluid samples are not only scarce in number but also tend to be heterogenic in terms of genome, transcriptome and especially function. For instance, cancer metastasis is an inefficient process, only very few tumor cells disseminating into the body fluid can ultimately succeed in forming a metastasis focus, most of the tumor cells in the body fluid no longer have activity and metastasis capacity due to anoikis. Therefore, even if these tumor cells are not significantly different in the genome aspect, obviously they are not identical in the functional aspect, which directly influence success of the metastasis and clinical outcome of the patient. One important subject in clinical cancer research is to find tumor cell subgroups capable of inducing a distant metastasis. These tumor cells can survive in the body fluid such as blood, pleural effusion, cerebrospinal fluid and the like and can effectively form the distant metastasis, thus conducting a functional evaluation and a further typing on the rare tumor cells in the body fluid is crucial, and the purpose of the typing is to investigate malignant degree and metastatic potential of the tumor cell subgroups having different functional characteristics, and accordingly to further conduct a prognostic judgement for the patient.

Identifying the rare tumor cells and conducting a functional evaluation in a complex biological liquid sample is a very challenging work. The tumor cell being rare means that it is necessary to adopt a detecting method with single cell precision. At present identifying exfoliative tumor cell in the body fluid sample mainly depends on cytologic examination, conducting an identification based on morphological characteristics of the tumor cells, and further ascertaining organ source and pathological typing thereof in conjunction with immunohistochemistry. It is slow and laborious and has high professional requirements. In 2011, Professor Robert A. Weinberg of Massachusetts Institute of Technology in USA summarized ten basic characteristics of tumor cells ("Hallmarks of Cancer: The Next Generation", Cell, 2011, 144, 646), including maintaining proliferation signal, escaping from growth inhibition, inhibiting cell death, infinite self-replication, inducing angiogenesis, activating infiltration metastasis, avoiding immunological injury, promoting tumor inflammation, abnormal energy metabolism and genomic instability and the like. These basic characteristics can effectively identify the malignant cells, but most of them are related with function, wherein except for the characteristics of "abnormal energy metabolism", other characteristics are all difficult to conveniently conduct high-throughput detection on single cell scale.

A tumor cell has an energy metabolic pathway different from a normal cell, this phenomenon was firstly observed by Otto Warburg. Warburg found that, even in the presence of oxygen, the tumor cell still conducted an energy metabolism mainly in a glycolysis mode, the glucose uptaken by it was much higher than the normal cell. Such an effect is referred to as Warburg effect Warburg accordingly won the Nobel prize of 1931. Warburg effect has been widely used in clinic, by using a glucose analog with a radioactive label (18F-FDG, namely 2-fluoro-2-deoxy-D-glucose, FDG for short) as a tracer, and applying a positron emission tomography (PET/CT), one can noninvasively, visually and sensitively detect a malignant tissue with in vivo high glucose uptake, so as to find a tumor in situ and a metastasis focus. In an in vitro detection, it is likewise able to identify a malignant tumor cell by using the radio-labeled glucose analog, meanwhile it is also able to conduct a detection by using a fluorescein-labeled glucose analog. Further research found that, the tumor cell has a variety of nutrient sources, besides glucose, it is also particularly addicted to glutamine, thus it is able to detect different metabolism modes of the tumor cell by different metabolic markers.

Therefore, how to implement high-throughput detection on a large number of cells, and identifying the rare tumor cells by detecting the energy metabolism of all the cells in the body fluid sample, especially further conducting typing on these tumor cells based on the metabolism mode thereof, have very important theoretical and practical significances.

SUMMARY

The purpose of the invention is to provide a method for effectively and rapidly detecting energy metabolism mode and intensity of rare tumor cells in a cancer patient's body fluid sample, and to conduct functional typing for them based on the energy metabolic characteristics of the tumor cells with high metabolic activity, wherein different functional subgroups have different malignant degrees and metastatic potentials, thus it is able to further conduct a prognostic judgement and a survival time prediction for the cancer patient based on the number of the cells in different functional subgroups.

The invention is directed to one subgroup of the rare tumor cells in the cancer patient's body fluid sample, namely the tumor cells with high metabolic activity. It is well known that, the cells in a tumor tissue exfoliate in situ and disseminate into the body fluid, such as blood, pleural effusion, peritoneal effusion, cerebrospinal fluid and the like, this can form an instant metastasis of the tumor. But meanwhile, metastasis is an inefficient process, only very few tumor cells disseminating into the body fluid can ultimately succeed in forming a metastasis focus, most of the tumor cells in the body fluid no longer have activity and metastasis capacity due to anoikis. An object concerned by the invention is the tumor cell with high metabolic activity in the body fluid sample. In the previous patent applications (Application Number: 201610285622.2), we proposed that it is able to identify the tumor cells with high glucose uptake in the body fluid sample by using a fluorescein labeled glucose analog (such as 2-NBDG). Because the malignant tumors have a variety of energy sources, glucose is the most common one among them, the tumor cells with high glucose uptake are also the most common subgroup in the tumor cells, but there are still tumor cells which use other energy source and adopt other energy metabolism mode. The purpose of this patent application is not to identify the tumor cells by a metabolic marker, but to respectively count the number of the tumor cells with high metabolic activity having different energy metabolism modes by using two types of different metabolic markers, this number represents the number of the tumor cell subgroups having different energy metabolism modes or different malignant degrees and metastatic potentials in the body fluid sample, it can be used in prognostic judgement and survival time prediction of the cancer patient. The content of the invention is illustrated in detail below.

Because the radio-labeled glucose analog FDG has been widely used in clinical detection of a malignant tissue with in vivo high glucose uptake, but the radio-labeled glucose analog has a low spatial resolution and it is radioactive, thus it is difficult to be used in an in vitro high-throughput detection of glucose uptake capacity on a large number of cells. The invention uses the fluorescein-labeled glucose analog (such as 2-NBDG) in the in vitro high-throughput detection of the glucose uptake capacity on a large number of cells. On the other hand, the invention also introduces other metabolic markers for characterization of other energy metabolism modes of the tumor cells except for glucose, such as redox marker, i.e. resazurin that are used in detection of a large number of reducing substances which are accumulated at the time of tumor cell glycolysis. In this way, the number of two types of tumor cells having high metabolic activities and mainly based on glucose metabolism and non-glucose metabolism can be counted. Meanwhile, the invention also introduces a leukocyte common antigen anti-CD45 as exclusion marker, its function is on one hand to exclude most of leukocytes in the sample, on the other hand to determine positive cut-off values of 2-NBDG and resazurin by fluorescence values of 2-NBDG and resazurin of anti-CD45 positive leukocyte, so as to identify the tumor cell with high metabolic activity.

In the present invention, the tumor cells with high metabolic activity are divided into two functional subgroups by 2-NBDG and resazurin. They respectively adopt different energy metabolism modes, wherein one group is anti-CD45 negative and 2-NBDG positive, it mainly uses glucose as energy source of the tumor cells, another group is anti-CD45 negative, resazurin positive, 2-NBDG negative, it mainly uses an energy substance except for glucose as energy source of the tumor cells, the numbers of the cells in these two groups reflect malignant degree and metastasis capacity of the in situ tumor, they can be used in prediction of prognosis and survival time for a cancer patient.

A specific method is briefly described: after removal of erythrocyte, incubating a small amount of body fluid sample (1 to 10 mL, such as blood, pleural effusion or cerebrospinal fluid) with fluorescein-labeled glucose analog 2-NBDG, resazurin and fluorescein labeled anti-CD45 antibody, then spreading all the cells onto a chip including hundreds of thousands of micropores, conducting a multichannel fast imaging by using a high content equipment, and further determining the positive cut-off values of 2-NBDG and resazurin by a program analysis, so as to identify all anti-CD45 negative, 2-NBDG or resazurin positive cells as the tumor cells with high metabolic activity, and finally conducting typing for these tumor cells with high metabolic activity according the fluorescent characteristics of 2-NBDG or resazurin, simply dividing them into two groups of cells, one group is anti-CD45 negative, 2-NBDG positive (high uptake) subgroup, and another group is anti-CD45 negative, resazurin positive (high uptake), 2-NBDG negative (low uptake) subgroup.

Through single cell sequencing, it can be firstly proved that these anti-CD45 negative, 2-NBDG or resazurin positive tumor cells with high metabolic activity are indeed tumor cells. We take out these cells with high metabolic activities one by one by micromanipulation equipment to conduct the single cell DNA sequencing, which mainly comprises a detection of driver gene mutation and a detection of copy number variation (CNV). The experiment results indicate that, for a lung adenocarcinoma patient's blood, pleural effusion and cerebrospinal fluid sample, in more than 70% of suspected tumor cells, a driver gene mutation (EGFR, KRAS and the like) consistent with the in situ tumor cell is detected, the remaining cells without the driver gene mutation can also be determined as tumor cells by copy number variation. In some of the samples which are negative in a traditional cytologic examination or unable to be confirmed, this method can effectively find the tumor cells and confirm them by sequencing. The tumor cells with high metabolic activity which are screened out based on the metabolic marker have high activity, they are the tumor cells having metastatic potential, but the tumor cells having different energy metabolic characteristics are not different in terms of the driver gene mutation, but a further copy number variation analysis shows that these two tumor cell subgroups with different energy metabolism modes are different in terms of amplification and deletion of gene, this means that they are different in terms of metastatic potential, drug resistance and the like.

The method for identifying and typing the tumor cells based on energy metabolism mode adopted by the invention, namely high uptake of glucose or resazurin and the cell surface doses not express leukocytes common antigen anti-CD45 are common characteristics of the tumor cells, without depending on size of tumor cells, surface antigen expression and the like, thus it is a simple and fast method for identifying the tumor cells, and can further classify the rare tumor cells having different energy metabolic characteristics based on the uptake characteristics for glucose or resazurin. The method adopted by the invention conducts a fast detection for a large number of cells by using a high-speed fluorescent imaging system, thus enable an enrichment of the rare tumor cells of in the body fluid sample, namely it is able to detect all karyotes in the body fluid sample, so as to avoid loss of the rare tumor cells caused by the enrichment step. Meanwhile the uptake of glucose and resazurin as well as the detection of cell surface membrane protein anti-CD45 do not influence the cell activity, it can be used in the subsequent sequencing of single cell genome, transcriptome as well as in vitro culture and other applications. Arranging the cells in an addressable manner can conveniently find and take out the tumor cells.

The inventors complete the present invention on the basis of the above-mentioned findings.

A first aspect of the present invention provides a method for detecting and typing rare tumor cells in a body fluid sample, comprising the following steps:

(Step A) incubating karyotes in the body fluid sample with a first metabolic marker capable of producing a fluorescence signal and a second metabolic marker capable of producing a fluorescence signal;

(Step B) detecting the fluorescence signal of the metabolic marker for all the cells by means of high-throughput imaging, so as to determine energy metabolism mode and intensity of the cells; and (Step C) identifying and typing the tumor cells in the body fluid sample according to the fluorescence signal of a metabolic marker combination;

where, the first metabolic marker capable of producing the fluorescence signal is fluorescein labeled glucose analog, preferably 2-NBDG, and the second metabolic marker capable of producing the fluorescence signal is resazurin.

The metabolic marker capable of producing the fluorescence signal means that the marker is labeled by a fluorophore and can be uptaken largely by the tumor cells, or the marker itself does not produce the fluorescence signal but can largely react with a metabolism related molecule in the tumor cells and converts to a state capable of producing the fluorescence signal. The invention adopts a combination use of two metabolic markers of fluorescein labeled glucose analog with resazurin. High uptake amount of the fluorescein labeled glucose analog indicates that malignant degree and metastatic potential of the tumor cells are high. High uptake amount of the resazurin indicates that malignant degree and metastatic potential of the tumor cells are high.

Preferably, the body fluid sample is one selected from the group consisting of blood, pleural effusion, peritoneal effusion and cerebrospinal fluid.

Preferably, in step A, the incubation time of karyotes and the metabolic marker capable of producing the fluorescence signal is from 2 minutes to 2 hours, more preferably from 5 minutes to 30 minutes.

In another preferred example, step A also comprises adding a fluorescein labeled antibody against leukocytes surface common antigen, to recognize leukocytes, so as to distinguish the tumor cells from leukocytes.

Preferably, the fluorescein-labeled antibody against the leukocyte surface common antigen is allophycocyanin, anti-CD45-APC, namely allophycocyanin (APC) labeled anti-CD45 antibody. The fluorescence carried by the fluorescein labeled antibody against the leukocyte surface common antigen and the fluorescence carried by the metabolic marker capable of producing the fluorescence signal do not interfere with each other.

In another preferred example, step A also comprises adding a bovine serum albumin, to block the cells and the microwell chip, so as to further eliminate nonspecific adsorption to the fluorescein labeled glucose analog (such as 2-NBDG).

In another preferred example, in step A, the rare tumor cells in the tumor patient's body fluid sample can be enriched, to increase concentration of the tumor cells, the enrichment method includes but is not limited to antibody labeled immunomagnetic bead, filtration membrane and the like. For example, the rare tumor cells in the body fluid sample can be enriched by immunomagnetic bead method, wherein the immunomagnetic bead is loaded with an antibody specifically binding to the tumor surface antigen or an antibody specifically binding to the leukocyte surface antigen.

In another preferred example, in step A, the karyotes in the body fluid sample are added to the microwell array chip, making the karyotes to enter into the micropores, so as to ensure that the cells are not lost at the time of the high-throughput imaging detection.

In another preferred example, step B also comprises comparing with a reference value or a standard curve, so as to qualitatively or quantitatively determine the level of metabolic activity of the tumor cells.

In another preferred example, step C also comprises typing the tumor cells on the basis of the difference between the tumor cell energy metabolic characteristics displayed by two or more metabolic markers.

A second aspect of the invention provides a kit for detecting and typing rare tumor cells in a body fluid sample, the kit includes:

(a) a microwell array chip, the chip includes multiple micropores for accommodating the cells and can be addressed;

(b) a first metabolic marker capable of producing a fluorescence signal;

(c) a second metabolic marker capable of producing a fluorescence signal; and (d) a fluorescein labeled antibody against the leukocyte surface common antigen, used in labeling leukocytes in the sample.

Preferably, the first metabolic marker capable of producing the fluorescence signal is a fluorescein-labeled glucose analog, preferably 2-NBDG, the second metabolic marker capable of producing the fluorescence signal is resazurin, the fluorescein labeled antibody against the leukocyte surface common antigen is Allophycocyanin (APC) labeled anti-CD45 antibody. The fluorescence carried by the above-mentioned antibody against the leukocyte surface common antigen and the fluorescence carried by the first metabolic marker and second metabolic marker capable of producing the fluorescence signal do not interfere with each other.

Preferably, the number of the micropores on the microwell array chip is from 5 thousand to 500 thousand, more preferably from 150 to 250 thousand.

In another preferred example, the bottom of the micropores on the microwell array chip is closed or has one hole with a size not exceeding 5 pin.

Compared with the prior art, the present invention has the following benefits:

(a) The method according to the present invention can cost effectively, rapidly, and accurately detect the energy metabolism mode of very small number of tumor cells in the body fluid sample and conduct a functional typing on them. The method according to the present invention can not only count the tumor cells having metabolic activity, but also recognize the tumor cells having high activity and malignancy, providing a basis for further molecular detection against these tumor cells.

(b) The present invention ensures that a very small number of the tumor cells are not lost in whole metabolic activity detection process by means of the microwell array chip, this is a bottleneck of the rare cells detection. Because the identifying method is simple and can be combined with the high-speed fluorescent imaging system, it can rapidly screen a large number of cells, enabling direct identification of the rare tumor cells in a complex sample without the enrichment. A traditional rare tumor cell enriching method is complicated in operation and more tumor cells are lost, whereas the method according to the present invention abandons the traditional method in which firstly enriching the rare tumor cells in blood or pleural effusion then detecting them, by using a large number of addressable micropores accommodating all the cells, and by using a fast and simple fluorescein-labeling method and a high-speed fluorescent imaging, in order to rapidly identify the rare tumor cells from very large number of cells, the whole operation is simple and fast, and because there is no enrichment, very few tumor cells are lost. In addition, the method according to the present invention directly identifies the tumor cells having high activity and malignancy, and provides a good basis for subsequent further molecular detection such as sequencing.

(c) The present invention provides a characterization method for function of the rare tumor cells. These tumor cells exfoliating into the body fluid from the in situ tumor tissue not only represents molecular characteristics of the in situ tumor focus, but also are direct source of the tumor instant metastasis. Even if these rare tumor cells have similar genomic characteristics, they themselves have huge functional heterogeneity, being manifested in activity, malignant degree, and metastatic potential, for instance wherein much portion of the tumor cells are in apoptosis state, and a small portion of the tumor cells having high activity and metastatic potential can ultimately form a metastasis focus. Directly conducting a functional characterization on the rare tumor cells in the body fluid sample contributes to knowing the state of a primary tumor and evaluating their malignant degree and metastatic potential. The present invention provides a typing against energy metabolism mode of the rare tumor cells which is simple to detect, cheap, reliable, and can further conduct a typing of energy metabolism mode for them, in order to count the tumor cells having characteristic energy metabolism mode and intensity and conduct a further molecular detection, such as detection of the genome and transcriptome.

DETAILED DESCRIPTION

Figure 1:
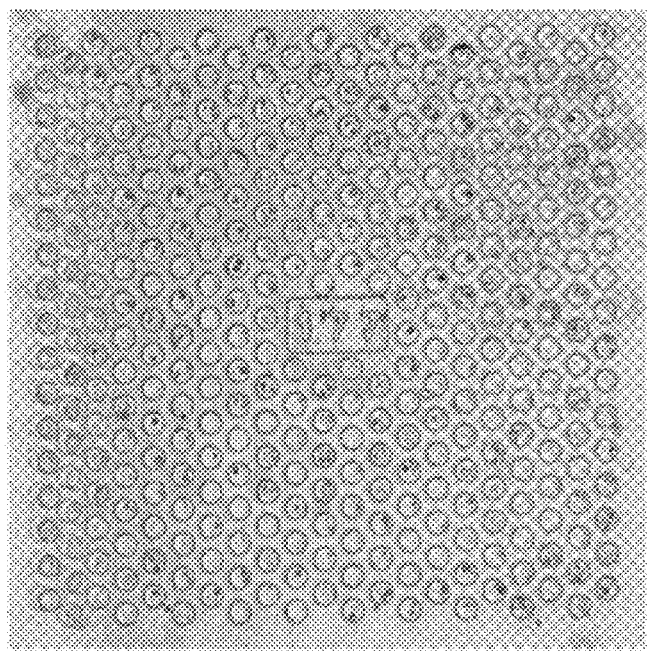
FIG. 1 shows a microphotograph of a certain numbered area on one microwell array chip, the purpose of the numbering is to conveniently locate the cells on the chip. The microwell array chip has 400 to 2500 groups of such numbered areas, in total 100000 to 500000 micropores.

The inventors, through extensive and deep researches, firstly develop a method for detecting the rare tumor cells in the patient's body fluid sample based on the energy metabolism mode and conducting functional typing to them, whereas the tumor cells having different energy metabolism modes have different malignant degrees and metastatic potentials.

Researches indicate that the feature of the tumor cell metabolism is to replace oxidative phosphorylation of normal tissue cells with high level of aerobic glycolysis. Because of low efficiency of glycolysis, the tumor cells need to uptake a large number of glucose. Further researches find that besides glucose, the tumor cells may also have other energy substance source, such as glutamine, a large number of reductive enzymes are accumulated in the cells. In the present invention, the rare tumor cells in the body fluid sample are identified according to a biological principle namely the capacity of uptaking glucose or the capacity of reducing resazurin by the tumor cells is much higher than the normal cells. In order to increase specificity of the identification, in the present invention of the leukocyte is further excluded by using the leukocyte surface marker anti-CD45. Because 2-NBDG and resazurin can both produce the fluorescence signal, a very large number of cells can be identified within a short time with the help of a high-speed fluorescence imaging equipment, thus the invention is not required to firstly conduct a complicated enrichment process on the rare tumor cells in the body fluid sample like the reported method. For the body fluid sample such as pleural effusion and cerebrospinal fluid, because of its low total cell number, the detection can be directly conducted without enriching the tumor cells. For a blood sample, the number of the cells can be reduced by a magnetic sphere negative selection of a simple labeled CD45 antibody after lysis and removal of erythrocytes, then the detection is conducted. If the blood sample is less or the CTC number is more, the detection can be directly conducted without the negative selection.

The method described in the present invention has similarities with a tumor imaging detection method for detecting glucose uptake by the tissue with a radioactive glucose analog ($^{18}$F-FDG, 2-fluorine-18-fluoro-2-deoxy-D-glucose) which has been used in clinic. $^{18}$F-FDG is transported into the cells by a glucose transporter, and phosphorylated under the action of hexokinase, to generate 6-PO$_4$-$^{18}$F-FDG and accumulate in the cells and can be detected by Positron Emission computed Tomography (PET). Therefore, the PET imaging based on the radioactive glucose analog $^{18}$F-FDG can be used to show site, morphology, size, number of the tumor and radioactive distribution within the tumor, in clinic it is mainly used in diagnosis of a malignant tumor and differential diagnosis of benign or malignancy, clinical staging, evaluating efficacy and monitoring recurrence and the like. The vast majority of the benign focuses do not uptake or slightly uptake $^{18}$F-FDG. In clinic, uptake amount of $^{18}$F-FDG by the focus is measured by using a half dose therapy of SUV (standard uptake value), and benign and malignancy of the tissue are identified, generally SUV>2.5 is considered as a malignant tumor, SUV<2.0 can be considered as a benign lesion.

For the tumor cells, they have various different phenotypes, genetic characteristics and metabolism modes. In the present invention, two or more metabolic markers are used to collectively detect the characteristic metabolism mode of the tumor cells, these metabolism modes are closely related to the malignant degree and the metastatic potential; compared with other molecular characteristics, it is able to more simply and reasonably reflect the malignant degree and the metastatic potential of the tumor cells.

Terminology

As used herein, "2-NBDG" refers to 2-(N-(7-nitrobenz-2-oxa-1,3-diazol-4-yl)amino)-2-deoxyglucose, which is a glucose analog with a fluorescent label, and can be used in detecting uptake of glucose by the cells.

"Resazurin" refers to 7-hydroxy-3H-phenoxazin-3-one 10-oxide, its English name is Resazurin, it is a blue dye having only a weak fluoresce, but it can be irreversibly reduced to a resorufin having a strong red fluorescence, and can be used in detecting the reductive enzyme within the cells.

"2-NBDG high uptake" means that the amount of 2-NBDG uptaken by the cells is higher than the mean value of the amounts of 2-NBDG uptaken by the leukocyte in the sample plus five folds of the standard deviation.

"Resazurin high uptake" means that the amount at which the cells reduce resazurin uptaken by them into a fluorescent form is higher than the mean value of the amounts of resazurin uptaken and reduced by the leukocytes plus three folds of the standard deviation.

The preferred examples of the invention are given below in conjunction of the accompanying drawings, in order to illustrate the technical solution of the invention in detail. For the experiment methods in which the specific conditions are not indicted in the following examples, they generally follow the conventional conditions, for example the conditions described in Sambrook et al., Molecular cloning: laboratory manual (New York: Cold Spring Harbor Laboratory Press, 1989), or follow the conditions recommend by the manufacturer. Unless otherwise specified, percentage and part are weight percentage and weight part. In the examples, all culture mediums, cell lines, and antibodies are all commercially available.

EXAMPLES

Detection of 2-NBDG and resazurin uptaken by rare tumor cells in a lung cancer patient's pleural effusion sample One micorporouse array PDMS chip is provided, its structure is as shown in FIG. 1, it includes 400 numbered areas, each area includes about 350 micropores with a diameter of 25 μm, in total 14 thousand micropores, and they can accommodate about 600 thousand karyotes.

In this example, the method comprises the following steps:

(1) 5 ml of lung cancer patient's pleural effusion was centrifuged (500 g, 5 minutes) and the cells were isolated, the erythrocyte was remove by using an erythrocyte lysate of BD Company, the cells were resuspended with a Hank's balanced salt solution (HBSS) and washed, finally resuspended in 500 ml of HBSS;

(2) 2 ml of Allophycocyanin (APC) labeled anti-CD45 antibody was added into 500 ml of cell suspension (about 1 million cells) which is then turned over on a turnover instrument and incubated for 1 hour;

(3) the 500 ml of cell suspension is centrifuged, a supernatant was discarded, then the cells were diluted with HBSS, and a cell suspension was dripped onto two microwell array chips, standing for 10 minutes, a microscopic bright field picture of the chip is as shown in FIG. 1, the cells were substantially in the micropores, but because some of the leukocytes were small in size, there were more than one cells in some of the micropores;

(4) the solution on the chip surface was removed, and fluorescein labeled glucose analog 2-NBDG (400 μM) and resazurin (1 μM) were added onto each chip, standing in an incubator of 37° C. for 15 minutes;

(5) after completion of the incubation, the chip was washed with an ice PBS for 8 times, and imaged with a high-speed fluorescent imaging equipment, and fluorescence values of 2-NBDG, resazurin and anti-CD45 of each cell were recorded.

Figure 2:
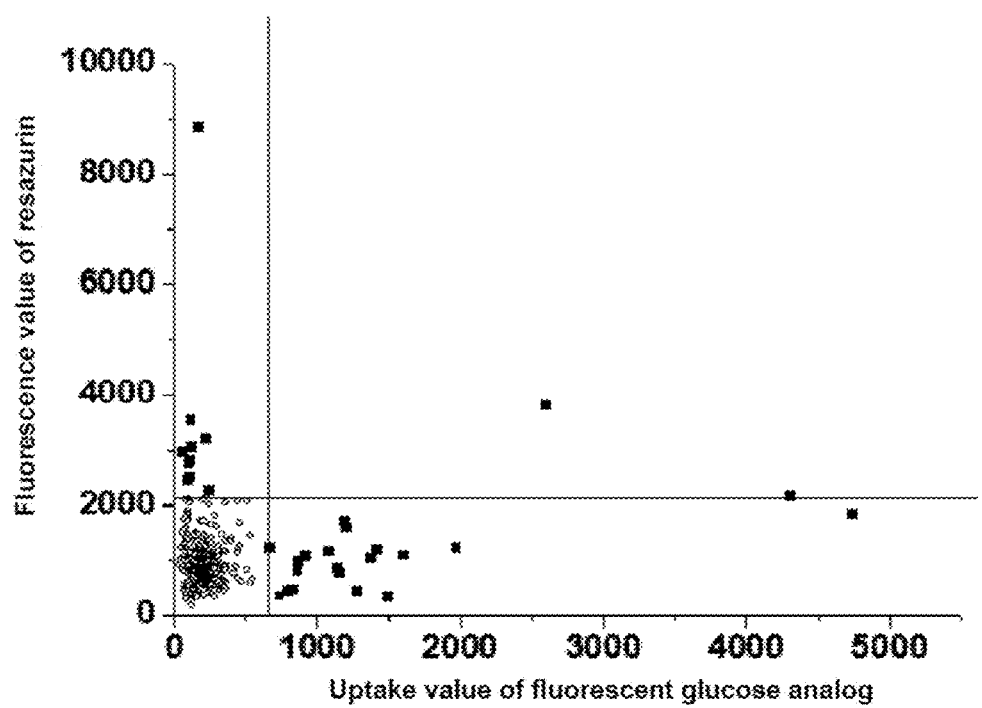
FIG. 2 shows a scatter diagram of uptake fluorescence values of 2-NBDG and resazurin of all the anti-CD45 negative cells on one chip according to examples of the present invention, in this figure two straight lines respectively represent the cut-off values of 2-NBDG and resazurin high uptake, wherein the method for determining the cut-off value of 2-NBDG is the mean value of the 2-NBDG uptake values of the anti-CD45 positive cells plus 5 folds of a standard deviation, the method for determining the cut-off value of resazurin is the mean value of the resazurin uptake values of anti-CD45 positive cells plus 3 folds of the standard deviation.

Cut-off values of 2-NBDG and resazurin can be calculated according to the fluorescence values of 2-NBDG and resazurin in anti-CD45 positive leukocyte, if higher than this cut-off value the cells are cells with high metabolic activity. FIG. 2 shows a scatter diagram of the uptake values of 2-NBDG and resazurin in all anti-CD45 negative cells, the anti-CD45 negative cells can be divided into 4 subgroups according to the cut-off values, namely a cell subgroup of anti-CD45 negative/resazurin being high, a cell subgroup of anti-CD45 negative/2-NBDG being high, a cell subgroup of anti-CD45 negative/resazurin, 2-NBDG being both high, a cell subgroup of anti-CD45 negative/resazurin, 2-NBDG being both low. Wherein, a definition of resazurin and 2-NBDG high uptake has been illustrated in the "terminology". The cells in the first three subgroups (the cell subgroup of anti-CD45 negative/resazurin high, the cell subgroup of anti-CD45 negative/2-NBDG high, the cell subgroup of anti-CD45 negative/resazurin, 2-NBDG being both high of) were taken out one by one to conduct a single cell sequencing and conduct an in situ tissue comparison, it was found that most of these cell had EGFR 19del mutation consistent with the in situ tissue, wherein 7 cells among 10 cells of anti-CD45 negative/resazurin high had the EGFR 19del mutation, 16 cells among 20 cells of anti-CD45 negative/2-NBDG being high had the EGFR 19del mutation, 3 cells among 4 cells of anti-CD45 negative/resazurin, 2-NBDG being both high had the EGFR 19del mutation. These cells having the EGFR 19 del mutation were all the tumor cells, whereas 8 cells in which the EGFR19del mutation was not detected were found having a large fragment of gene amplification and deletion by means of genome copy number variation detection, conforming to the characteristics of the tumor cells. In the cells of anti-CD45 negative/resazurin, NBDG being both low, a large proportion of them are not the tumor cells, and a large number of cells are unable to successfully conduct the single cell genome sequencing, this may be related to the fact of the cells being in an apoptosis state.

The cells with two different metabolism modes were found in multiple lung cancer patient samples, their number and relative proportion were not identical, a further genome copy number variation analysis on the tumor cells with two kinds of metabolism modes found that these two types of tumor cells were different in terms of copy number variation, specifically manifested in that the cells with glucose high uptake generally had amplification of PIK3CA gene and deletion of PTEN gene, whereas the cells with resazurin high uptake tended to have amplification of MYC gene. Such a difference in the genome aspect reflect the difference between the two types cells in signaling pathway activating mode and the differences in terms of metastatic potential and drug resistance and the like.

At present, in clinic, by using a radioactive substance which can be phagocytized or swallowed by the tumor cells, by applying a PET imaging of the radioactive substance in showing site, morphology, size, number of the tumors and radioactive distribution within the tumor, in clinic the invention are mainly used in diagnosis of malignant tumor and differential diagnosis of benign and malignancy, clinical staging, evaluating efficacy and monitoring the recurrence and the like.

The present invention quantitatively detects the glucose uptake capacity of the rare tumor cells by a labeled glucose analog, such as fluorophore labeled D-glucose analog 2-NBDG which has a metabolic pathway similar to D-glucose. The fluorophore labeled D-glucose analog 2-NBDG enters into the cells via a glucose transporter (GLUT), then C-6 position of which is phosphorylated by a hexokinase. Researches have shown that, compared with a benign cell, 2-NBDG can be rapidly uptaken by a malignant tumor cell, thereby becoming an optical marker for detecting the malignant tumor cell.

Some of the tumor cells also have other source of energy substance, but glycolytic process with high intensity makes a large number of reductive enzymes to accumulate within the tumor cells, these enzymes can rapidly reduce a resazurin without fluorescence signal to an oxidized form with fluorescence signal, so as to quantitatively characterize the amount of the reductive enzymes within the cell, thereby to detect the intensity of glycolysis.

The invention, based on the glucose analog having fluorescence signal and a glycolysis-related reductive enzyme detection method and kit, detects energy metabolism mode and intensity of the very rare tumor cells in the tumor patient's body fluid sample, so as to conduct a typing of energy metabolism function on these tumor cells, thereby to effectively select the tumor cells with high malignant degree and great metastatic potential.

It should be understood that, the above-mentioned examples are merely used to illustrate the invention but not to limit the protection scope of the invention, one skilled in the art can make various variations or modifications in the invention based on the principle disclosed by the invention and the disclosed content, these equivalent forms likewise fall into the protection scope of the appended claims.

What is claimed is:

1. A method for detecting and typing tumor cells with high metabolic activity in a body fluid sample, comprising:
    step A, incubating karyotes from the body fluid sample with a fluorescein-labeled first metabolic marker, a fluorescein-labeled second metabolic marker, and a fluorescein-labeled anti-CD45 antibody, wherein the first metabolic marker is 2-(N-(7-nitrobenz-2-oxa-1,3-diazol-4-yl)amino)-2-deoxyglucose (2-NBDG), and the second metabolic marker is resazurin;
    step B, detecting fluorescence signals generated by the fluorescein labels associated with the karyotes by high-throughput imaging so as to determine energy metabolism; and
    step C, identifying tumor cells with high metabolic activity in the body fluid sample which are the karyotes having fluorescence signals of both of the metabolic markers stronger than corresponding positive cut-off values of 2-NBDG and resazurin and not having fluorescence signal of the anti-CD45 antibody.

2. The method according to claim 1, wherein the body fluid sample is selected from the group consisting of blood, pleural effusion, peritoneal effusion and cerebrospinal fluid, and wherein the incubation is for a time of from 2 minutes to 2 hours.

3. The method according to claim 1, wherein the cut-off value of 2-NBDG is a mean value of 2-NBDG fluorescence signal values of all anti-CD45 positive cells plus 5 folds of standard deviation, and the cut-off value of resazurin is a mean value of resazurin fluorescence signal values of all the anti-CD45 positive cells plus 3 folds of standard deviation.

4. The method according to claim 1, wherein step A further comprises adding the fluorescein-labeled karyotes from the body fluid sample into a microwell array chip, the microwell array chip including multiple addressable microwells for accommodating cells.

5. The method according to claim 1, wherein step A further comprises enriching tumor cells in the body fluid sample.

6. A kit for detecting and typing tumor cells in a body fluid sample, wherein the kit comprising:
    (a) a microwell array chip, including multiple addressable microwells for accommodating cells;
    (b) a fluorescein-labeled first metabolic marker capable of producing a fluorescence signal;
    (c) a fluorescein-labeled second metabolic marker capable of producing a fluorescence signal; and
    (d) a fluorescein-labeled anti-CD45 antibody;
    wherein the first metabolic marker is 2-(N-(7-nitrobenz-2-oxa-1,3-diazol-4-yl)amino)-2-deoxyglucose (2-NBDG), and the second metabolic marker is resazurin.

7. The kit according to claim 6, wherein the number of the microwells on the microwell array chip is from 5 thousand to 500 thousand, and the bottom of the microwells on the microwell array chip is closed or has one or more micropores with a diameter of from 5 μm to 10 μm.

* * * * *